US006855489B1

(12) United States Patent
Herman et al.

(10) Patent No.: US 6,855,489 B1
(45) Date of Patent: Feb. 15, 2005

(54) SYSTEMS AND METHODS FOR REMOVING VIRAL AGENTS FROM BLOOD

(75) Inventors: Robert E. Herman, Lindenhurst, IL (US); John Chapman, Lake Villa, IL (US); Chong-Son Sun, Lake Forest, IL (US); Jean M. Mathias, Lillois (BE); Veronique Mayaudon, Gognies-Chaussee (FR); Serge de Gheldere, Hoeilaart (BE); Daniel F. Bischof, McHenry, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/688,079

(22) Filed: Oct. 13, 2000

Related U.S. Application Data

(62) Division of application No. 08/742,572, filed on Oct. 28, 1996, now Pat. No. 6,190,855.

(51) Int. Cl.$^7$ .......................... A01N 1/02; A61K 35/16; A61M 1/14
(52) U.S. Cl. .......................... 435/2; 435/975; 424/526; 424/529; 424/530; 424/532; 424/534; 210/782; 210/749; 422/44
(58) Field of Search ..................... 435/2, 975; 424/526, 424/530, 532, 529, 534; 422/44; 210/782, 749

(56) References Cited

U.S. PATENT DOCUMENTS

| | | |
|---|---|---|
| 3,876,738 A | 4/1975 | Marinaccion et al. |
| 4,025,618 A | 5/1977 | Garber et al. |
| 4,150,744 A | 4/1979 | Fennimore |
| 4,246,107 A | 1/1981 | Takenaka et al. |
| 4,340,479 A | 7/1982 | Pall |
| 4,396,382 A | 8/1983 | Goldhaber |
| 4,439,179 A | 3/1984 | Lueders et al. |
| 4,473,474 A | 9/1984 | Ostreicher et al. |
| 4,548,605 A | 10/1985 | Iwamoto et al. |
| 4,673,504 A | 6/1987 | Ostreicher et al. |
| 4,701,267 A | 10/1987 | Watanabe et al. |
| 4,708,803 A | 11/1987 | Ostreicher et al. |
| 4,711,793 A | 12/1987 | Ostreicher et al. |
| 4,767,541 A | 8/1988 | Wisdom |
| 4,900,449 A | 2/1990 | Kraus et al. |
| 4,915,683 A | 4/1990 | Sieber |
| 4,925,572 A | 5/1990 | Pall |
| 4,964,990 A | 10/1990 | Kraus et al. |
| 4,985,153 A | 1/1991 | Kuroda et al. |
| 4,997,577 A | 3/1991 | Stewart |
| 5,023,052 A | 6/1991 | Nagatomo et al. |
| 5,076,935 A | 12/1991 | Kraus et al. |
| 5,089,146 A | 2/1992 | Carmen et al. |
| 5,092,996 A | 3/1992 | Spielberg |
| 5,100,564 A | 3/1992 | Pall et al. |
| 5,102,407 A | 4/1992 | Carmen et al. |
| 5,108,607 A | 4/1992 | Kraus et al. |
| 5,126,054 A | 6/1992 | Matkovich |
| 5,128,048 A | 7/1992 | Stewart et al. |
| 5,180,504 A | 1/1993 | Johnson et al. |
| 5,217,627 A | 6/1993 | Pall et al. |
| 5,229,012 A | 7/1993 | Pall et al. |
| 5,252,222 A | 10/1993 | Matkovich et al. |
| 5,269,946 A | 12/1993 | Goldhaber et al. |
| 5,288,403 A | 2/1994 | Ohno |
| 5,290,221 A | 3/1994 | Wolf, Jr. et al. |
| 5,298,165 A | 3/1994 | Oka et al. |
| 5,300,019 A | 4/1994 | Bischof et al. |
| 5,387,187 A | 2/1995 | Fell et al. |
| 5,399,268 A | 3/1995 | Pall et al. |
| 5,403,272 A | 4/1995 | Deniega et al. |
| 5,423,989 A | 6/1995 | Allen et al. |
| 5,476,587 A | 12/1995 | Kuroki et al. |
| 5,494,592 A | 2/1996 | Latham, Jr. et al. |
| 5,498,336 A | 3/1996 | Katsurada et al. |
| 5,498,340 A | 3/1996 | Granger et al. |
| 5,501,795 A | 3/1996 | Pall et al. |
| 5,512,187 A | 4/1996 | Buchholz et al. |
| 5,527,472 A | 6/1996 | Bellotti et al. |
| 5,536,238 A | 7/1996 | Bischof |
| 5,536,413 A | 7/1996 | Bormann et al. |
| 5,545,339 A | 8/1996 | Bormann et al. |
| 5,545,516 A | 8/1996 | Wagner |
| 5,549,834 A | 8/1996 | Brown |
| 5,591,337 A | 1/1997 | Lynn et al. |
| 5,601,727 A | 2/1997 | Bormann et al. |
| 5,607,579 A | 3/1997 | Latham, Jr. et al. |
| 5,639,376 A | 6/1997 | Lee et al. |
| 5,660,731 A | 8/1997 | Piechocki et al. |
| 6,319,662 B1 * | 11/2001 | Foley et al. ............... 435/2 |

FOREIGN PATENT DOCUMENTS

| | | |
|---|---|---|
| WO | WO95/19199 | 7/1995 |

* cited by examiner

Primary Examiner—Padmashri Ponnaluri
(74) Attorney, Agent, or Firm—Michael C. Mayo; Daniel D. Ryan; Andrew G. Kolomayets

(57) ABSTRACT

Systems and methods treat plasma carrying contaminants and cellular matter that are capable of entraining contaminants. The systems and methods separate cellular matter from the plasma by filtration, thereby removing contaminants entrained within the cellular matter. The system and methods add to the plasma a photoactive material. The systems and methods emit radiation at a selected wavelength into the plasma to activate the photoactive material and thereby eradicate the contaminant that is free of entrainment by cellular matter.

8 Claims, 11 Drawing Sheets

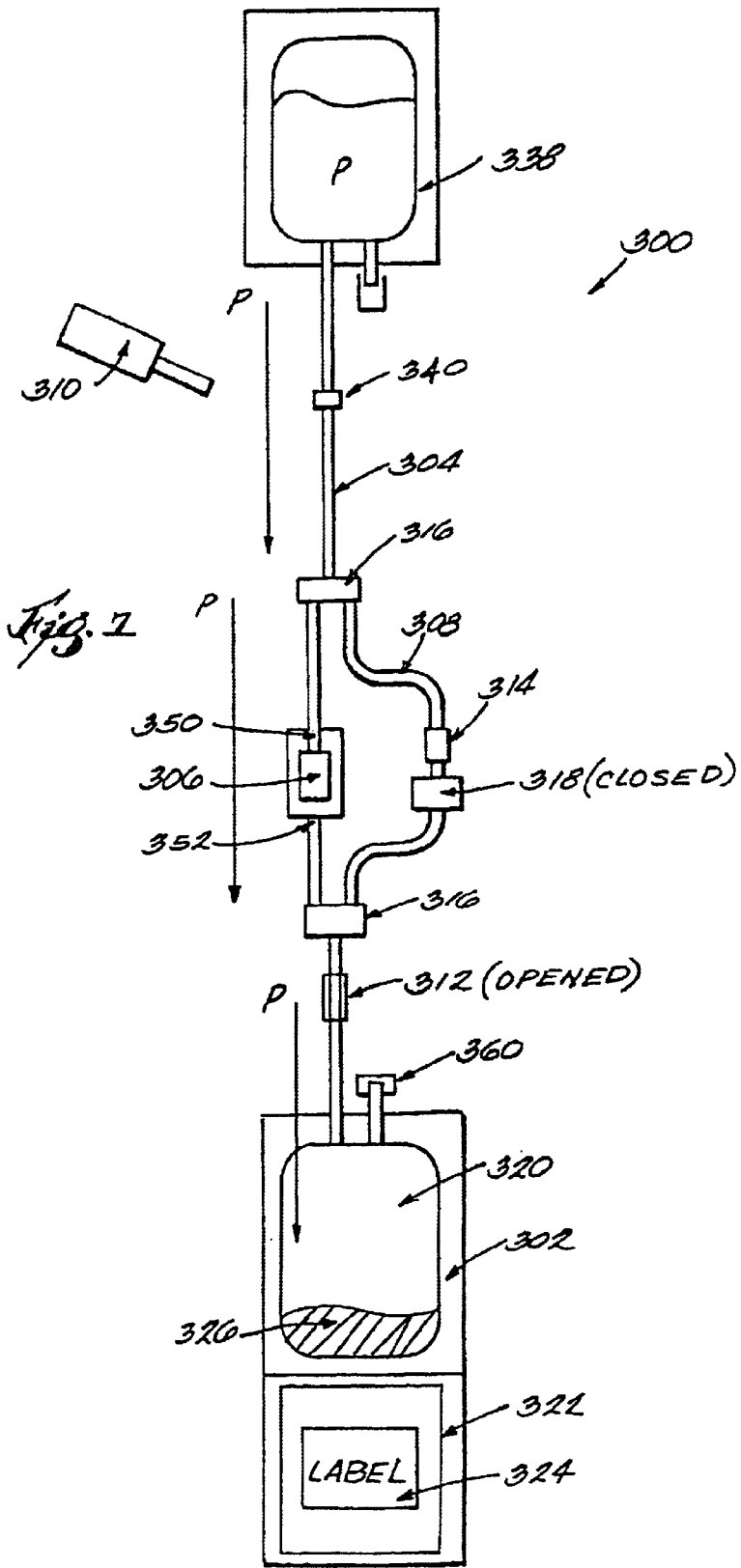

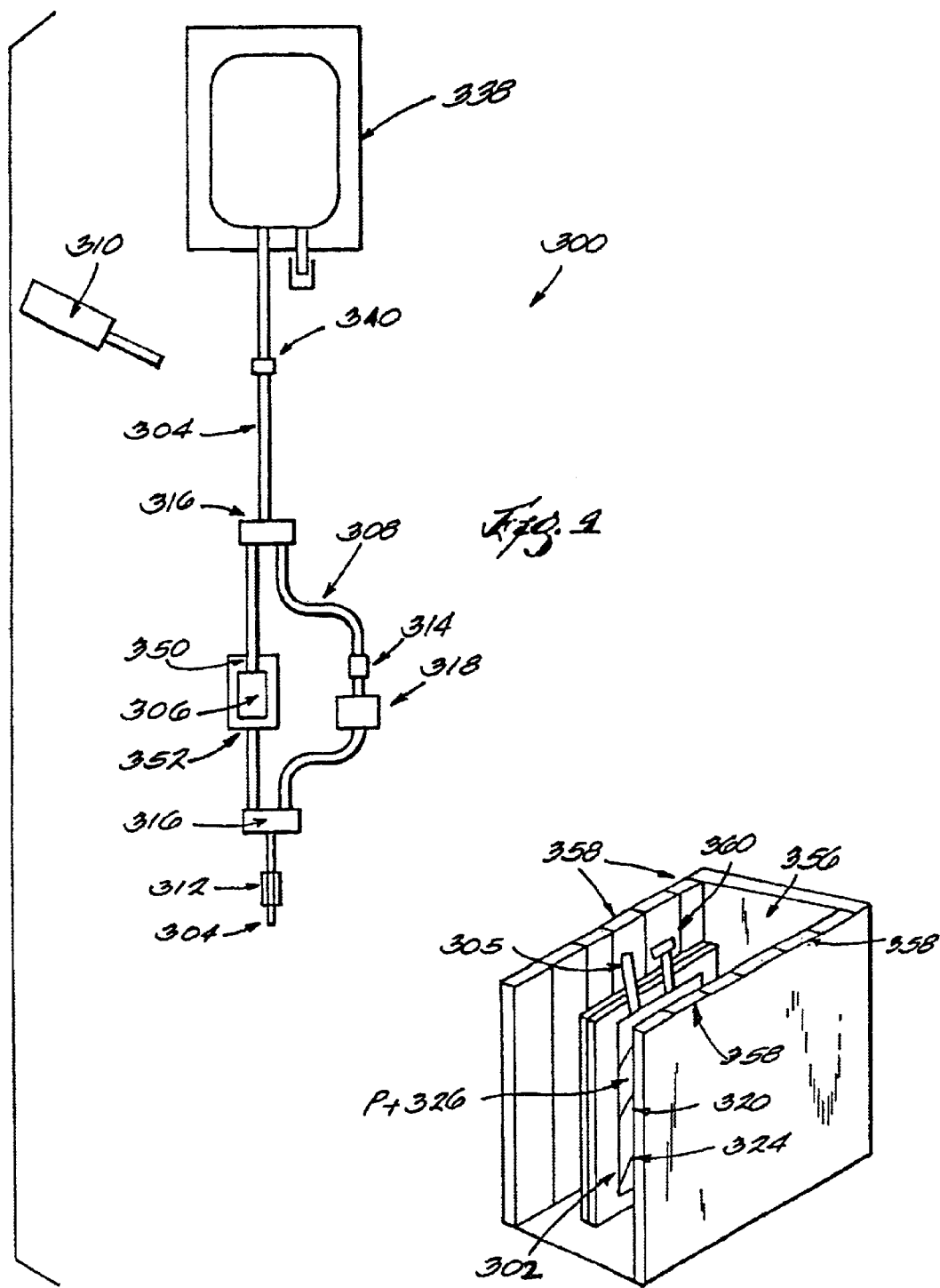

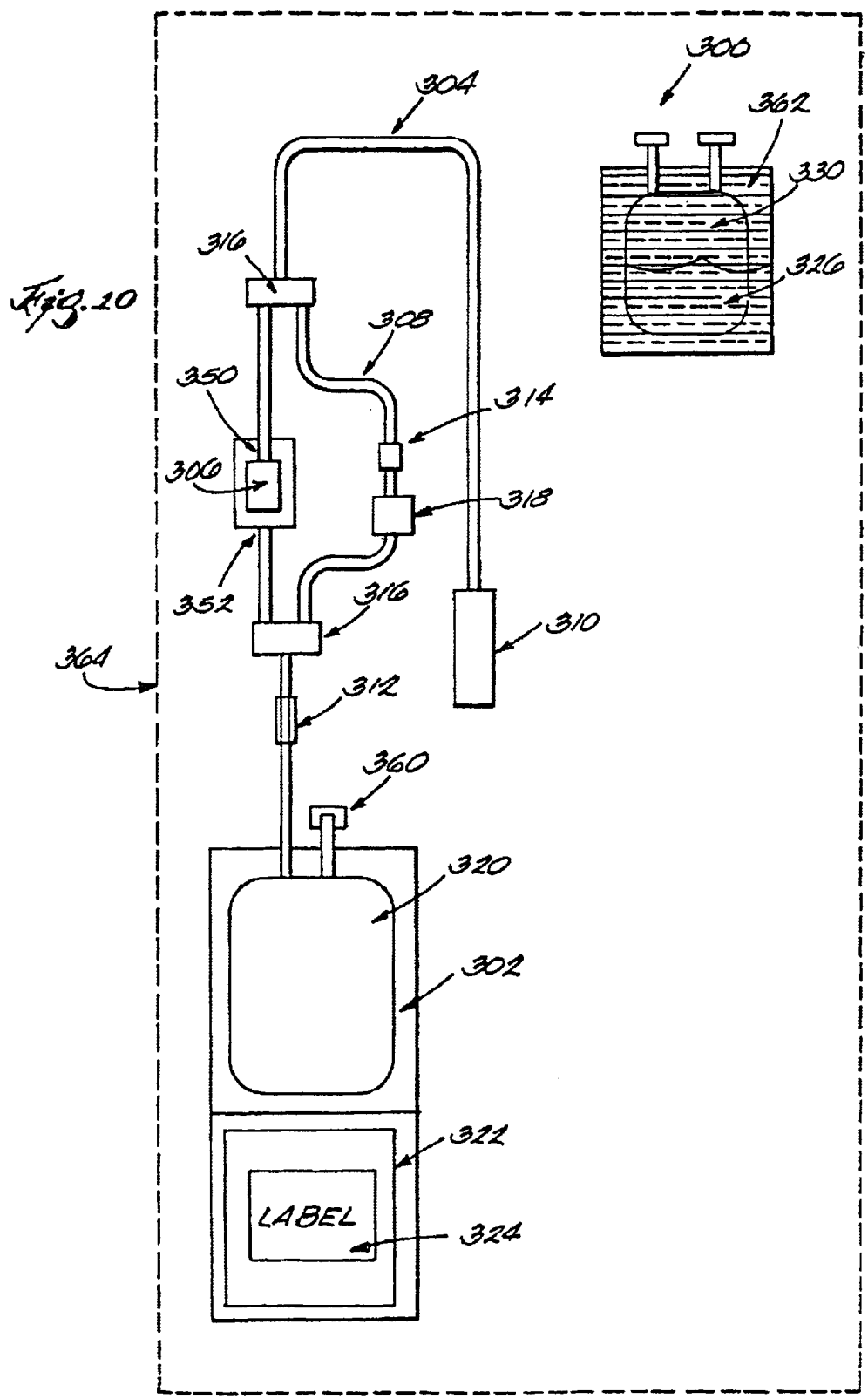

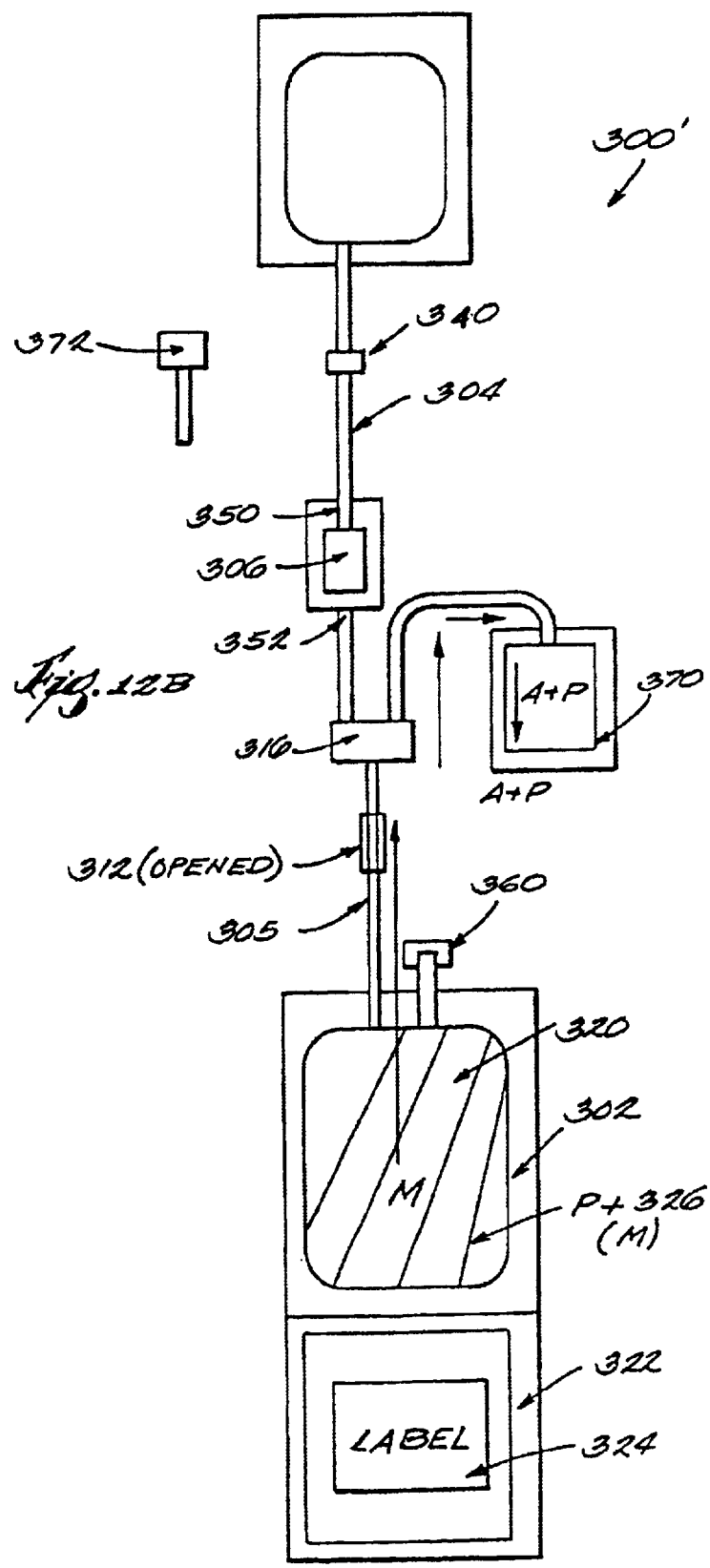

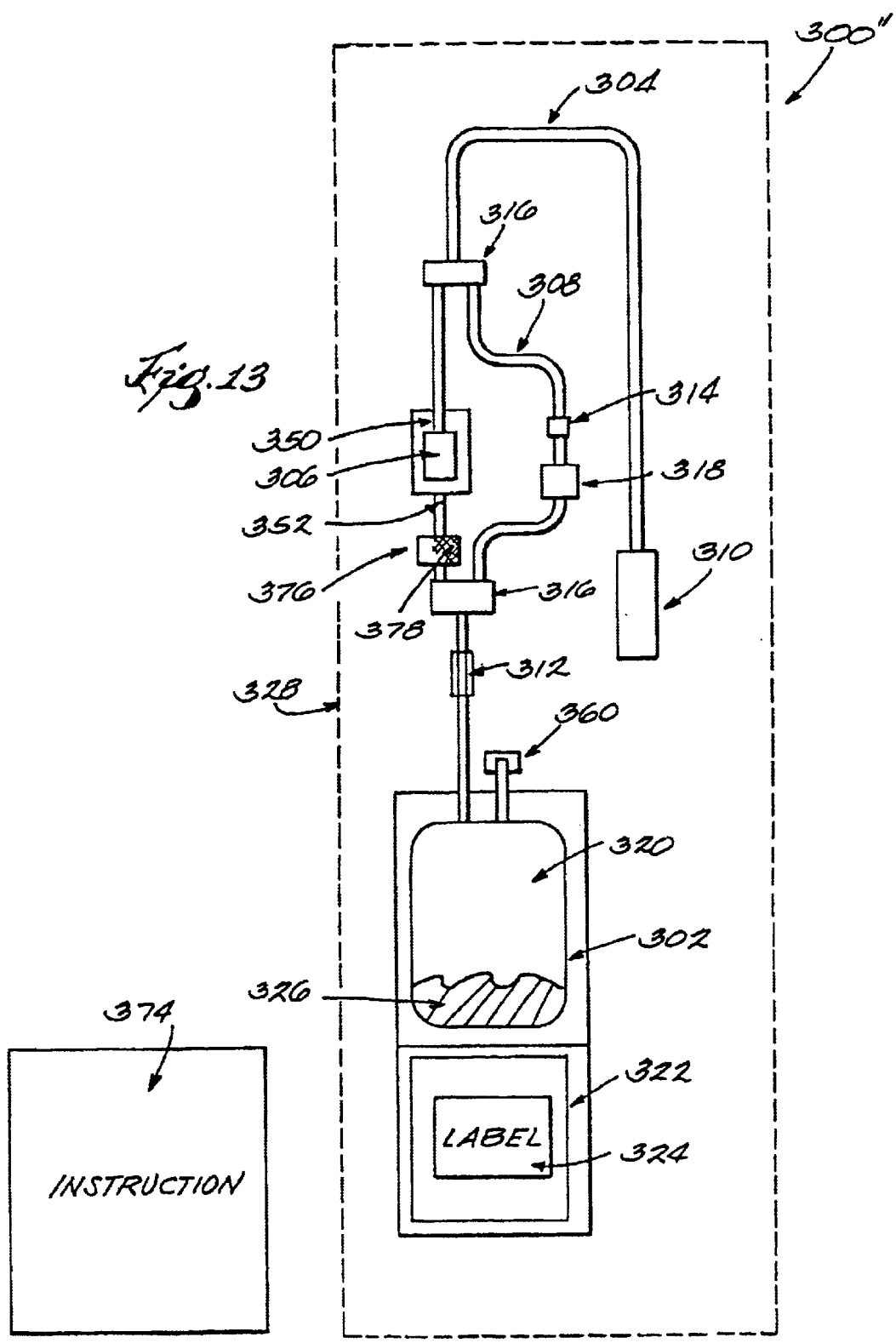

United States Patent 6,855,489 B1

SYSTEMS AND METHODS FOR REMOVING VIRAL AGENTS FROM BLOOD

RELATED APPLICATION

This application is a division of application Ser. No. 08/742,572 filed Oct. 28, 1996 now U.S. Pat. No. 6,190,855.

FIELD OF THE INVENTION

The invention generally relates to the eradication of contaminants using photodynamic therapy. The invention also generally relates to the processing of whole blood and its components for storage and transfusion. In a more specific sense, the invention relates to the extracorporeal treatment of collected whole blood and its components with photoactive materials to eradicate viruses and other pathogenic contaminants.

BACKGROUND OF THE INVENTION

With the coming of blood component therapy, most whole blood collected today is separated into its clinically proven components for storage and administration. The clinically proven components of whole blood include red blood cells, used to treat chronic anemia; platelet-poor plasma, from which Clotting Factor VIII-rich cryoprecipitate can be obtained for the treatment of hemophilia; and concentrations of platelets, used to control thrombocytopenic bleeding.

It is well known that blood can carry infectious agents like hepatitis-B virus; the human immunodeficiency (AIDS) virus; the Herpes virus; and the influenza virus. To avoid the transmission of these infectious agents during blood transfusions, donors of blood are routinely screened and also undergo serologic testing to detect the presence of these agents. Still, it is difficult to always assure that these infectious agents are detected.

The use of photodynamic therapy has been suggested as a way to eradicate infectious agents from collected blood and its components. Still, there has been a general lack of success in economically adapting the benefits of photodynamic therapy to the demands of the blood banking industry. One reason for this is that not all biological contaminants are carried free within the blood where they can be readily coupled to photoactive agents. Some biological contaminants are entrained on or within white blood cells out of the reach of photoactive agents.

For this and other reasons, the promise of photodynamic therapy in treating the nation's banked blood supply has gone largely unfulfilled.

SUMMARY OF THE INVENTION

The invention provides improved systems and methods for treating blood constituents to adventitious viral agents.

One aspect of the invention provides systems and methods which remove viral agents from plasma. The systems and methods remove from the plasma targeted cellular matter that does or might entrain viral agents. In a preferred embodiment, the targeted cellular matter includes leukocytes. The system and methods add to the plasma a photoactive material, which binds to viral agents that are free of entrainment by the targeted cellular matter. Radiation emitted at a selected wavelength into the plasma activates the photoactive material and thereby eradicates the free viral agents.

In a preferred embodiment, a system for treating plasma comprises tubing adapted to be coupled a plasma source, and a filter in the tubing to separate cellular matter from the plasma conveyed from the source. The system includes a transfer container coupled to the tubing to receive cellular matter-reduced plasma from the filter, and a source of photoactive material to be mixed with the plasma. In this embodiment, the tubing includes a path to vent air from the transfer container in a path that bypasses the filter.

In a preferred embodiment, systems and methods remove viral agents entrained within the cellular matter by conveying plasma in a first path through a filter. The systems and methods convey the cellular matter-reduced plasma from the filter in a second path, which includes a connected transfer container. The systems and methods mix the cellular matter-reduced plasma with a photoactive material within the transfer container, forming a plasma mixture.

In this embodiment, the systems and methods convey a portion of the plasma mixture from the transfer container in a flush path, which includes the second path, to thereby expose residual contaminants in the second path to the photoactive material. The systems and methods then separate the transfer container from the filter by severing the second path. After severance from the filter, a remnant of the second path remains attached to the transfer container. However, due to the prior flushing step, all contaminants in the attached second path remnant have been exposed to the photoactive material. Subsequent radiation of the transfer container thereby eradicates contaminants, which are free of entrainment by cellular matter, both within the transfer container and the attached second path remnant.

In a preferred embodiment, the flush path by passes the filter and also provides a path to vent air from the transfer container.

Another aspect of the invention provides systems and methods for treating plasma using multistage filtration, which targets for removal different species of cellular matter. The systems and methods separate a first species of cellular matter by filtration through a first filter media, thereby removing contaminants entrained within the first species of cellular matter. The systems and methods separating a second species of cellular matter by filtration through a second filter media, thereby removing contaminants entrained within the second species of cellular matter. The systems and methods add to the plasma a photoactive material and emit radiation at a selected wavelength into the plasma to activate the photoactive material, thereby eradicating the contaminant that is free of entrainment by cellular matter. In a preferred embodiment, the first filtration media targets leukocytes for removal, while the second filtration media targets platelets for removal.

Another aspect of the invention provides a kit that envelopes photoactive material in an overwrap that includes a light filtering material. The light filtering material absorbs light that activates the photoactive material. The presence of the light filtering material in the overwrap protects the photoactive material from photo-degradation due to absorption of ambient light during handling and storage prior to use.

In a preferred embodiment, the photoactive material within the kit includes methylene blue. In this embodiment, the light filtering material includes a blue material having phtalocyanine pigments.

In a preferred embodiment, the photoactive material is contained in liquid form within the kit. In this embodiment, the overwrap also includes material that reduces liquid vapor loss from the kit.

Other features and advantages of the invention will be pointed out in, or will be apparent from, the drawings, specification and claims that follow.

DESCRIPTION OF THE DRAWINGS

FIG. 7 is a plane view the kit shown in FIG. 1 being used to convey plasma from a source container, through the leukocyte reduction filter, and into the processing and storage container;

FIG. 9 is a perspective view of the kit shown in FIGS. 8A and 8B, after separation of the processing and storage container and placement of the processing and storage container in an irradiation chamber;

FIG. 10 is a plane view of an alternative embodiment of a blood processing and storage kit for reducing the presence of viral agents in plasma, in which the photoactive material is stored within an auxiliary container whose walls include a light filtering material;

FIG. 12B is a plane view of the kit shown in FIG. 12A being used to flush the tubing section next to the container with photoactive material, to assure exposure of residual viruses occupying the tubing section with photoactive material; and.

FIG. 13 is a plane view of another alternative embodiment of a blood processing and storage kit for reducing the presence of viral agents in plasma, which reduces the presence of viral agents in plasma by the removal by filtration of least two different cellular blood species which actually do or potentially can entrain viral agents.

Figure 1:
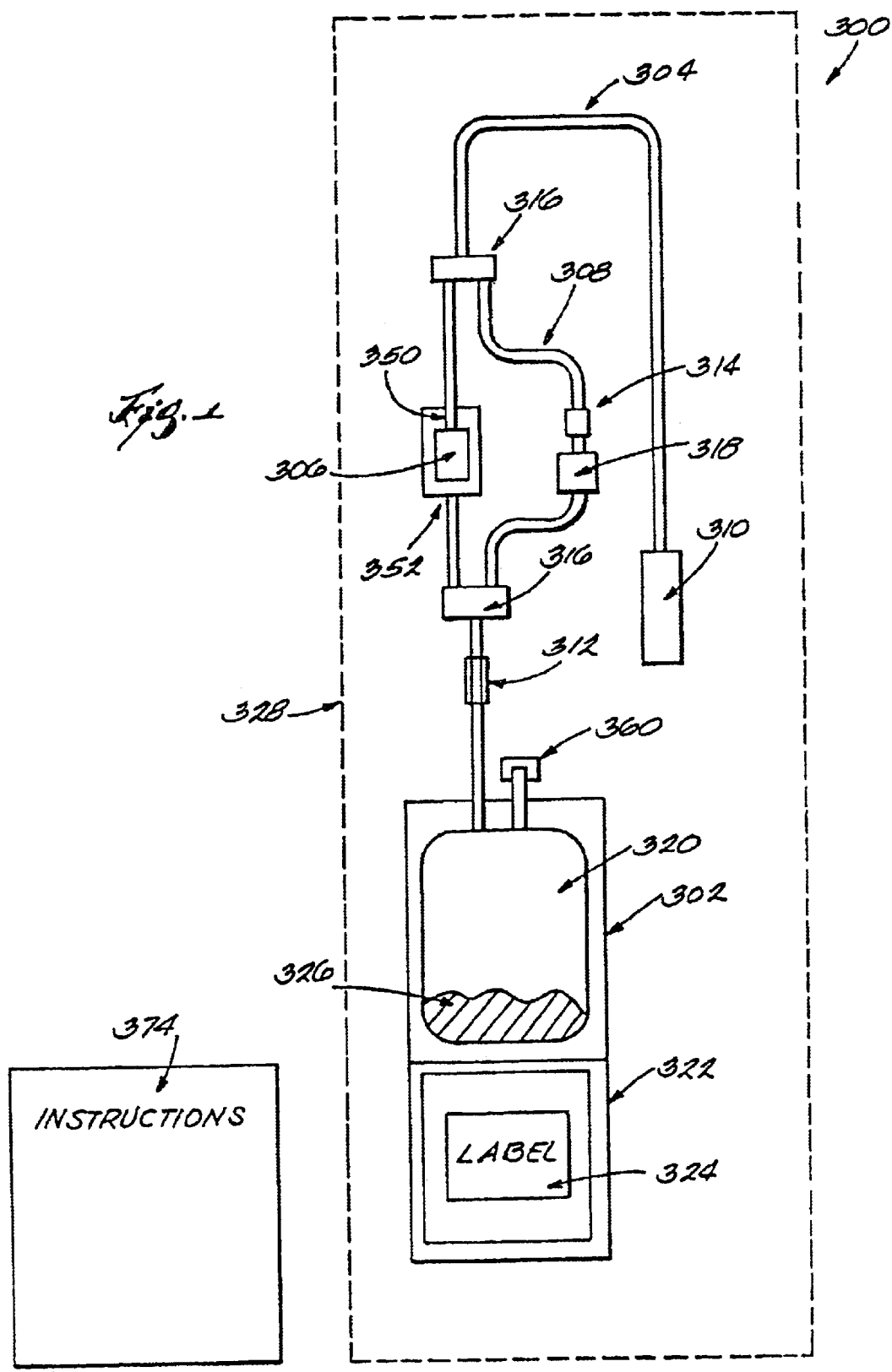
FIG. 1 is a plane view of a blood processing and storage kit for reducing the presence of viral agents in plasma.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

FIG. 1 shows a blood constituent processing and storage set or kit 300. The kit 300 is intended, during use, to assist in the removal of viral agents from plasma. The viral agents are either carried free within the plasma or are entrained on or within cellular matter (e.g., red blood cells, platelets, and leukocytes) that the plasma carries. The kit 300 shown in FIG. 1 will be described in the context of reducing the presence of viral agents in single donor units of plasma, because it is particularly well suited for this purpose.

The kit 300 includes a processing and storage container 302, which carries an integrally attached length of flexible transfer tubing 304. In the illustrated embodiment, the transfer tubing 304 is made from medical grade plasticized polyvinyl chloride plastic. However, other flexible medical grade plastic materials can be used.

The transfer tubing 304 includes an integrally attached in-line filter 306. The filter 306 includes a filter media 307 (see FIG. 5) that removes from plasma cellular matter that does actually or potentially entrain viral agents.

Figure 5:
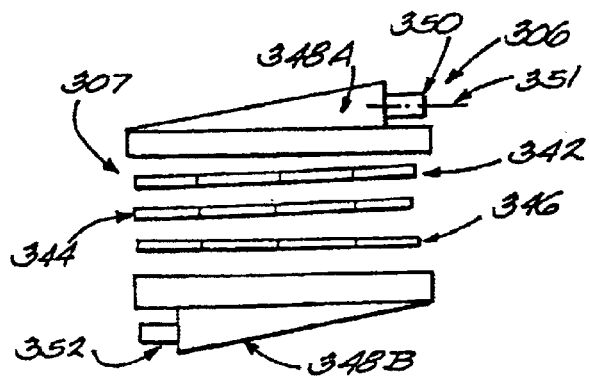
FIG. 5 is an exploded side view of the leukocyte reduction filter that forms a part of the kit shown in FIG. 1.

As FIG. 5 shows, the filter media 307 is encased within a two part housing 348A and 348B made, for example, from polycarbonate, although any engineering medical grade plastic with appropriate toxicology characteristics can be used. The housing 348A/348B is sealed about the filter media 307 by, for example, sonic welding.

The pore size of the filter media 307 can be tailored to remove by exclusion all or some species of cellular matter found in plasma, depending upon the extent to which viral agents sought to be eliminated are entrained by the different cellular species. In the illustrated embodiment, the principal cellular species targets of the filter 306 are leukocytes, for it is known that leukocytes entrain many viral agents. With this objective in mind, the filter media 307 comprises a non-fibrous membrane having a pore size smaller than the size of leukocytes, to thereby remove leukocytes by exclusion. In the illustrated embodiment, the media 307 also includes a prefilter material, which removes fibrin clots and other large size aggregates from the plasma.

The composition of the membrane for the media 307 can vary. For examples, hydrophilic membranes made from nylon, acrylic copolymers, polysulfone, polyvinylidene fluoride, mixed cellulose esters, and cellulose ester can be used to remove leukocytes by exclusion. Non-hydrophilic membranes can also be treated to serve as a membrane for the filter media 307. Likewise, the composition of the prefilter for the media 307 can vary. For example, the prefilter can comprise fibers of glass or polyester. Material selection takes into account customer preferences, performance objectives, and manufacturing requirements, including sterilization techniques.

In the illustrated and preferred embodiment, (see FIG. 5), the filter media 307 includes three filter media layers 342, 344, and 346. The first filter media layer 342 comprises USP Grade VI glass fiber or the equivalent. The second and third filter media layers 344 and 346 comprise polyethersulfone (PES) membranes, which remove leukocytes by exclusion. The second and third filter media layers 344 and 346 possess pore sizes which are approximately 10 fold smaller than the size of leukocytes and which decrease in the direction of flow. The second filter media layer 344 has a pore size in the range of about 0.9 $\mu$m to about 2.0 $\mu$m, with an average pore size of about 1.2 $\mu$m. The third filter media layer 346 has a smaller pore size in the range of about 0.3 $\mu$m to about 1.5 $\mu$m, with an average pores size of about 0.8 $\mu$m. The second and third filter media layers 344 and 346 also incidently remove red blood cells by exclusion.

The filter media 307 should preferably be capable of filtering 310 ml of plasma, suspended at a head height of 3 feet, in 20 minutes.

The housing part 348A includes an inlet 350, which, in use, conveys plasma and leukocytes into contact with the prefilter layer 342. The axis 351 of the inlet 350 is generally parallel to the plane of the layer 342 to uniformly perfuse plasma across the entire prefilter layer 342.

Figure 6:
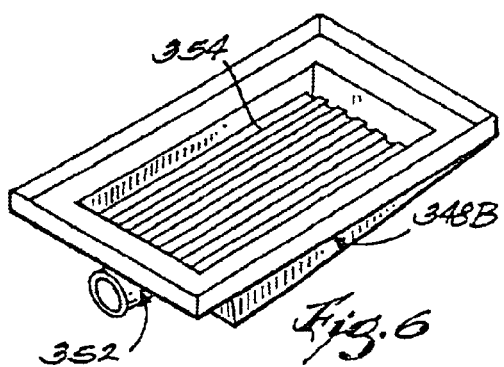
FIG. 6 is a top perspective view of the interior of the outlet housing part for the filter shown in FIG. 5.

The housing part 348B includes an outlet 352, which conveys leukocyte-reduced plasma from the second and third PES filter layers 344 and 346. As FIG. 6 shows, the interior surface of the housing part 348B is grooved, creating a fluid manifold 354 that uniformly distributes leukocyte-reduced plasma to the outlet 352.

Referring back to FIG. 1, a length of branch tubing 308 is integrally attached to the transfer tubing 304 by conventional Y-connectors 316. The branch tubing 308 forms a fluid path bypassing the filter 306. As will be described in greater detail later, the branch tubing 308 serves to vent air.

The far end of the transfer tubing 304 carries an air pillow 310. The air pillow 310 prevents collapse of the tubing 304 and 308 caused by pressure differentials during steam sterilization of the kit 300.

The transfer tubing 304 further includes a conventional in-line frangible cannula 312 between the filter outlet 352 and the processing and storage container 302. The cannula 312 normally closes fluid the transfer tubing 304 to fluid flow.

The cannula 312 can be constructed in various ways. U.S. Pat. Nos. 4,181,140 and 4,294,247 disclose representative constructions for the cannula 312, which are incorporated herein by reference. Alternatively, an external roller clamp or C-clamp of conventional construction could be used for the same purpose.

The branch tubing 308 includes a conventional in-line one-way valve 314. The valve 314 prevents fluid flow through the branch tubing 308 in the direction of the processing and storage container 302, while permitting fluid flow in the opposite direction away from the processing and storage container 302. For redundancy, the branch tubing 308 also includes an external roller clamp or C-clamp 328. The C-clamp 318 normally closes the tubing 308 between the one-way valve 314 and the processing and storage container 302.

The processing and storage container 302 can be constructed in various ways. In the illustrated and preferred embodiment, the container 302 includes an interior chamber 320. The transfer tubing 304 communicates with the chamber 320 for conveying plasma into the chamber 320. In a preferred implementation, the chamber 320 is capable of holding between 235 to 310 mL of plasma. A normally sealed outlet port 360 also communicates with the chamber 320. The port 360 is opened when it is time to remove plasma from the chamber 320.

The chamber 320 holds a photoactive material 326. The photoactive material 326 mixes with the plasma introduced into the chamber 320. The photoactive material 320 binds to extracellular viruses that plasma introduced into the chamber 326 may carry. When exposed to light energy in a particular spectrum, the photoactive material 326 inactivates the nucleic acids of the bound viruses, rendering them nonviable.

In the illustrated and preferred embodiment, the photoactive material 326 comprises 10 mL of liquid solution containing 83 micrograms of methylene blue in water at pH 3.1, without buffers or other additives. Methylene blue, a thiazine dye, possesses the ability to bind to nucleic acids with high affinity, targeting the viruses for destruction upon exposure to a particular spectrum of light energy. Methylene blue absorbs light in the 660 nm region of the visible spectrum, which is the spectrum region where plasma is most transparent. Methylene blue inactivates a broad range of viruses, such as HIV, human hepatitis B (HBV), human hepatitis C(HCV), and Parvo virus B19, with minimal loss of therapeutic plasma proteins.

The mixture of plasma and photoactive material 326 is irradiation by light within the chamber 320 as part of a viral inactivation process. The container 302 is therefore made of a material that is substantially transparent to the applied light energy. The material for the container 302 is also adapted to withstand contemplated storage conditions for the plasma.

In the illustrated and preferred embodiment, the applied light energy is in the white light spectrum (400 to 700 nm). The container 302 is therefore made of a plastic, poly (ethylene vinyl acetate) material. This material is transparent to white light and is also resistant to the cold temperatures at which frozen plasma is stored. This material is commercially available and is made and sold, for example, by Baxter Healthcare Corporation under the trademark PL-732® Plastic.

The container 302 also includes a flap 322, which extends below the chamber 320. The flap 322 carries a printed label 324 having identifying indicia. The flap 322 keeps the label 324 away from the chamber 320, where it could block or impede the irradiating light.

The container 302 also serves after the viral inactivation process to store the viral inactivated plasma at temperatures below −30° C., following standard blood banking procedures.

Further details of container 302 are found in copending U.S. patent application Ser. No. 08/121,820, filed Sep. 15, 1993, and entitled "Container for Irradiation of Blood Products."

Figure 4:
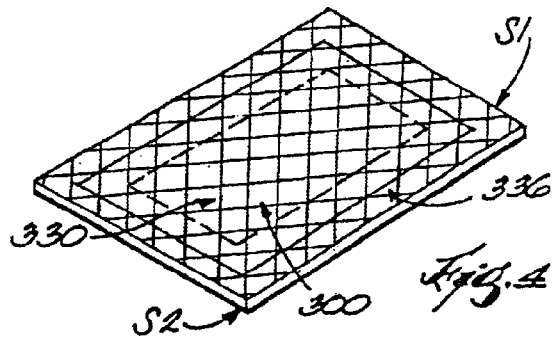
FIG. 4 is a top perspective view of the laminated walls of the overwrap envelope, after having been joined by a peripheral heat seal.

As FIG. 4 shows, the kit 300 is preferably enclosed for storage and handling before use in an overwrap envelope 328 (FIG. 1 diagrammatically shows the envelope 328 in phantom lines). The overwrap envelope 328 serves multiple functions.

To minimize evaporation of the liquid photoactive material 326 from the container 302 prior to use, the envelope 328 includes a material 332 possessing a relatively low water vapor transmission rate (WVTR). In the illustrated and preferred embodiment, the targeted WVTR is about 0.020 $g^{-1}$ at 25° C. and 60% relative humidity.

The particular composition of the water vapor barrier material 332 can vary. In the illustrated and preferred embodiment, the water vapor barrier material 332 comprises an oriented polypropylene material having a thickness of 25 μm.

To prevent degradation of the photoactive material 326 prior to use, the envelope also includes a light filtering material 330 possessing the ability to absorb ambient light energy in the spectrum that activates the photoactive material 326. It has been discovered that, during storage and handling prior to use, the photoactive material 326 absorbs from ambient visible light (400 nm to 700 nm) the spectrum that initiates photoactivation. The incidental absorption of ambient visible light by photoactive material 326 initiates a photoreduction process, creating byproducts that are either partially or completely ineffective for viral inactivation.

For example, exposure of methylene blue to visible ambient light (whose emission spectrum includes the 660 nm region) converts the methylene blue into colorless leucomethylene blue. The leucomethylene blue photoreduction byproduct is not effective in inactivating viruses.

The particular composition of the light filtering material 330 will vary according to the light sensitivity spectrum of the particular photoactive material 326 used. In the illustrated and preferred embodiment, the light filtering material 330 comprises a blue die of phtalocyanine pigments. The blue die material 326 transmits not more than 1% of light in the range of 600 nm to 700 nm, which is the spectrum in which methylene blue is activated.

Figure 2:
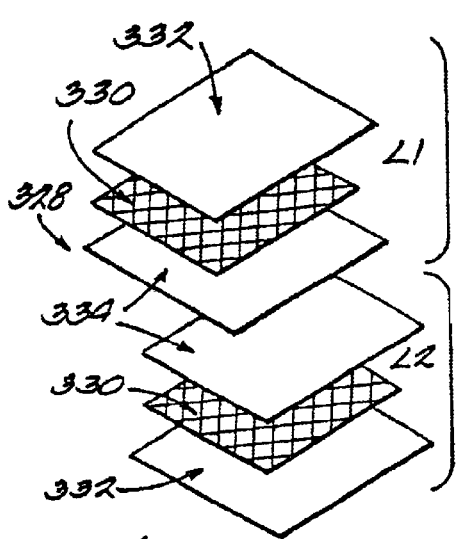
FIG. 2 is an exploded, perspective view of the laminated walls of the overwrap envelope shown in phantom lines in FIG. 1.
Figure 3:
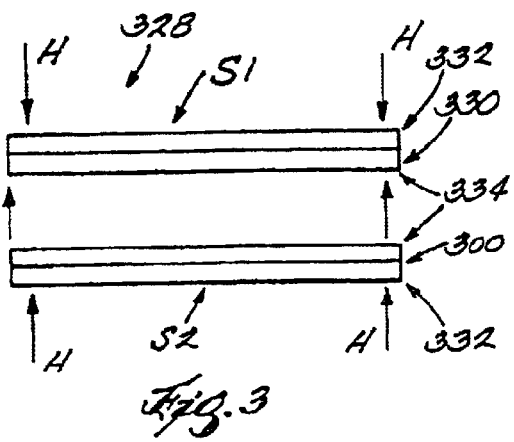
FIG. 3 is a side view of the laminated walls of the overwrap envelope shown in FIG. 2.

As FIGS. 2 and 3 show, in the illustrated and preferred embodiment, the overwrap envelope 328 comprises sheets S1 and S2, each of which comprises a multiple layer laminate L1 and L2. The water vapor barrier material 332 constitutes one of the exterior layers of each laminated sheet S1 and S2. The blue die comprising the light filtering material 330 is printed on the interior face of the water vapor barrier material 332.

Each laminated sheet S1 and S2 also preferably includes as another exterior layer a material 334 that flows in response to heat. The presence of the material 334 makes it possible to heat seal the two sheets S1 and S2 together, forming the envelope 328.

The particular composition of the heat flowing material 334 can vary. In the illustrated and preferred embodiment, the material 334 comprises a cast polypropylene material having a thickness of about 25 $\mu$m. The heat flowing material 334 can be attached to the layer 332, for example, by a polyurethane-polyester resin-epoxy.

Laminated sheets S1 and S2 as described, with the layers 330, 332, and 334 and suited for use as the overwrap envelope 328, can be purchased from Hosokawa Yoko Co., LTD. (Japan). The sheet material from this company has a weight of 50 g/m$^2$ and density 1.0 g/cm$^3$.

The envelope 328 is created by laying the sheets S1 and S2 of the overwrap laminate together (as FIG. 3 shows) and applying pressure and heat H along the sheet edges in a heat sealing die. The pressure and heat H form a peripheral heat seal 336, which joins the sheets S1 and S2 together, forming the envelope 328 (as FIG. 4 shows).

Despite the presence of the light filtering material 330, the overwrap envelope 328 as above described nevertheless retains sufficient transparency to other visible light spectrums to allow visual inspection of the contents of the overwrap envelope 328, for quality control or customer inspection purposes.

The overwrap envelope 328, including an appropriate light filtering material 330 as just described, can be used in association with other containers or in other systems which hold liquids or other materials sensitive to ambient light degradation. For example, photoactive materials 326 activated in different spectrum regions will require accordingly different light filtering material 330, For example, 4'-(4-Amino-2-oxa)butyl-4,5'8-trimethylpsoralen (S-59) is a photoactive material usable in conjunction with platelet-containing blood suspensions. S-59 is activated by ultraviolet-A light and can undergo intramolecular reactions when exposed to ambient UV-A and short wavelength regions of visible light. To protect against such degradation of S-59 material, the light filtering material 330 can comprise a UV-A absorbent red die.

For another example, as FIG. 10 shows, instead of using a light filtering overwrap envelope 328, the kit 300 (or another system) can include an auxiliary container 362 to store the light activated material 326 before use. The walls of the container 362 include an appropriate light filtering material 330 to protect the light activated material 326 from ambient light degradation before use. In this arrangement, the photoactivated material 326 is transferred from the auxiliary container 362 to plasma before the light activation process, either before or during filtration, or after filtration when the plasma occupies the processing and storage container 302. Of course, a container (like the container 302), which is intended to ultimately serve as a light transparent chamber, must remain free or essentially free of a light filtering material. In this arrangement, it is still desirable to provide an overwrap envelope 364 (shown diagrammatically in FIG. 10) to decrease water vapor loss of the liquid photoactive material 326 during storage and handling prior to use.

The overwrap envelope 328 (or 364 in the FIG. 10 embodiment) is torn away when it is time to use the kit 300. As FIG. 7 shows, a container 338 holding the plasma P is connected in a sterile fashion to the transfer tubing 304 near the air pillow 310. The source container 338 can, for example, hold fresh plasma or plasma that has been frozen and thawed. The plasma is harvested by conventional blood banking procedures. These procedures, which are accomplished through centrifugation of whole blood, yield plasma that is essentially free of red blood cells.

Known sterile connection mechanisms (not shown) like that shown in Spencer U.S. Pat. No. 4,412,835 can be used for connecting the container 338 to the transfer tubing 304. These mechanisms form a molten seal between tubing ends, which, once cooled, forms a sterile weld 340. The air pillow 310 is discarded after sterile connection between the source container 338 and the transfer tubing 304 is made.

As FIG. 7 shows, once the sterile connection is made, the source container 338 is suspended above the processing and storage container 302. The operator checks to assure that the clamp 318 is closed on the bypass branch tubing 308. The operator breaks the cannula 312, and the plasma P flows by gravity head pressure through the filter 306. The leukocyte-reduced plasma exits the filter 306 and drains into the chamber 320 of the container 302.

It has been observed that the triple layer membrane filter 306 described above provides plasma having a leukocyte level that is below the limit of flow cytometer detection (i.e., less than about one leukocyte per $\mu$L). The actual residual level of leukocytes in the plasma after filtration by the filter 306 is estimated not to exceed an average theoretical level of 0.004 leukocyte per $\mu$L. Based upon an initial leukocyte level of 0.79×10$^8$ per L, the leukocyte reduction percentage of the filter 306 is estimated to be about 99.99% (log reduction$\geq$4.0).

The methylene blue photoactive material 326 is mixed with the leukocyte-reduced plasma within the container 302 by manual inversion.

Figure 8A:
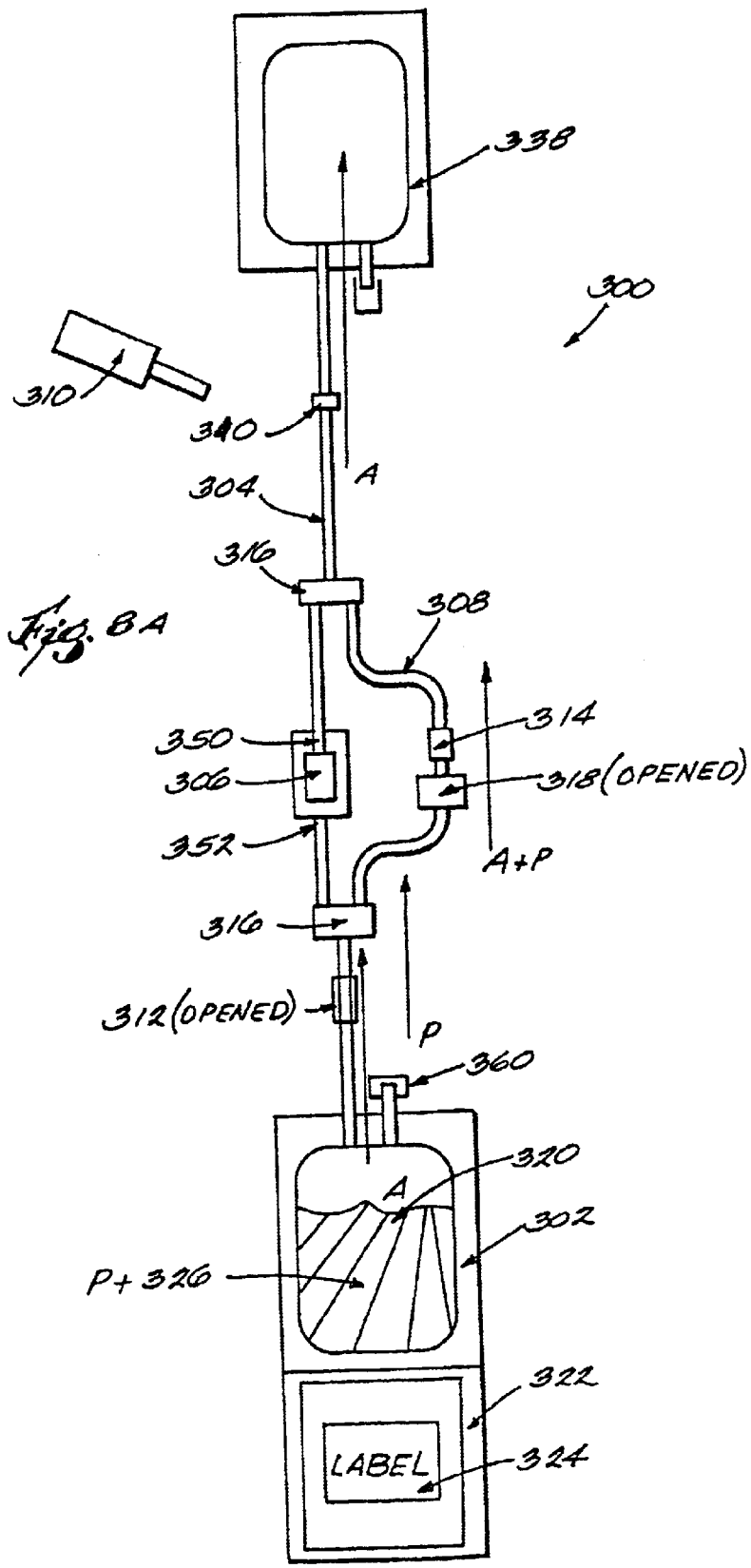
FIG. 8A is a plane view the kit shown in FIG. 7 being used to vent air and residual plasma from the processing and storage container in a bypass path around the leukocyte reduction filter.

As FIG. 8A shows, after mixing plasma P and photoactive material 326 within the container chamber 320, the clamp 318 is opened and the container 302 squeezed. Air A is vented from the container 302, through the bypass branch tubing 308 back into the source container 338. As FIG. 8A also shows, the venting of air A also displaces residual plasma P, out of the transfer tubing 304 between the filter 306 and the container 302 and into the bypass branch tubing 308. Viruses in the residual plasma P, having never entered the container chamber 320 have not been exposed to the photoactive material 326 and therefore should be removed before undertaking the desired photoactivation process.

Figure 8B:
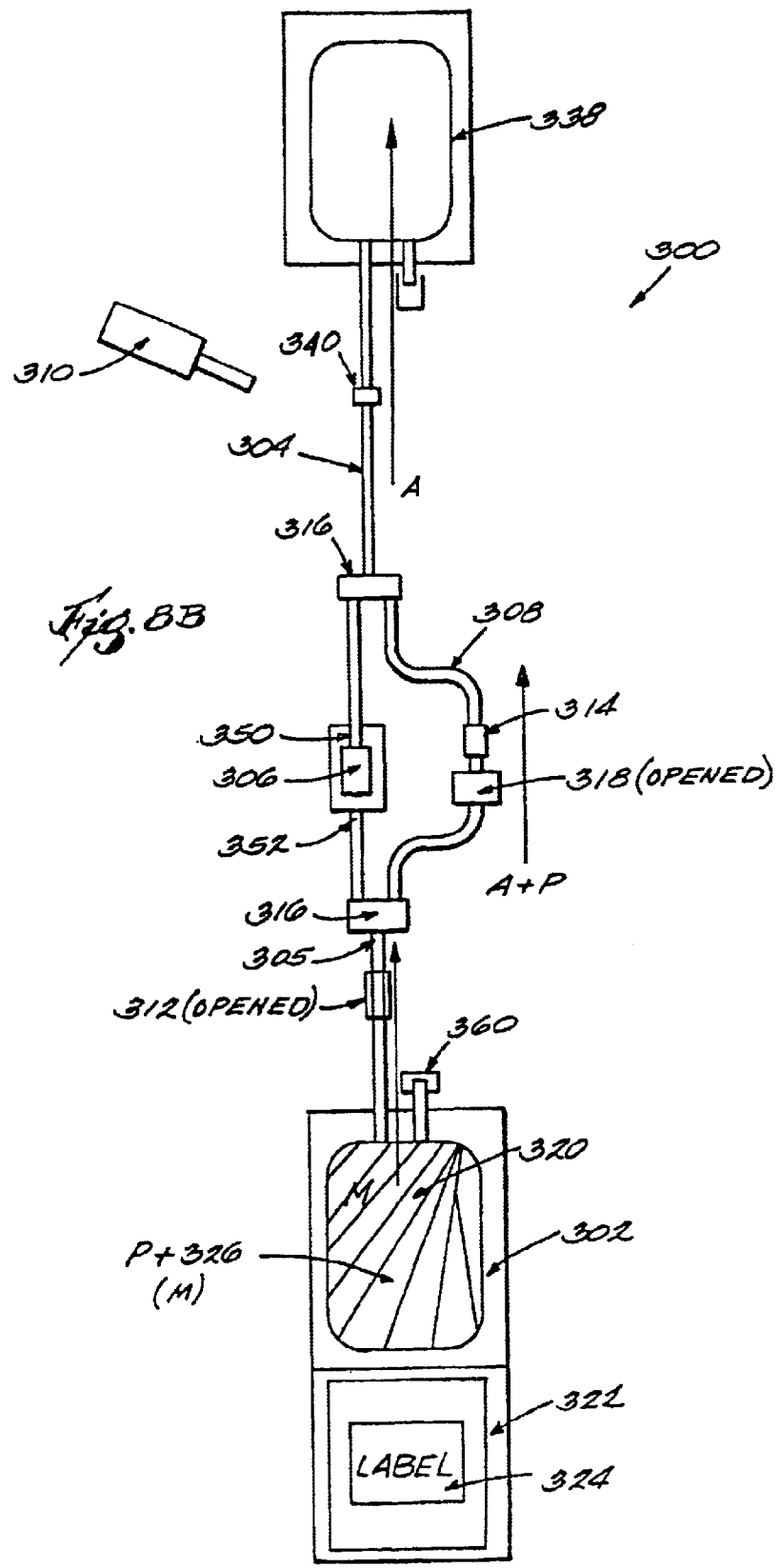
FIG. 8B is a plane view of the kit shown in FIG. 8A being used to flush the tubing section next to the container with photoactive material, to assure exposure of residual viruses occupying the tubing section with photoactive material.

As FIG. 8B shows, as air venting proceeds, an amount of the mixture M of photoactive material 326 and plasma P will enter the section 305 of the transfer tubing 304 between the filter 306 and the container 302. The mixture M is allowed to drain back into the container 302. The mixture M flushes this section of the transfer tubing 304 with the photoactive material 326 and plasma mixture. The flushing process assures that viruses still occupying this section of the tubing 304 after air venting will become mixed with the photoactive material 326. This assures that all viruses present in the container 302 and adjacent section 305 of tubing 304 are exposed to the material 326, to thereby assure the desired virucidal effect during subsequent exposure to light irradiation.

After air venting and flushing, as just described, the tubing 305 next to the container 302 is sealed closed using, for example, a dielectric tube sealer. As FIG. 9 shows, the remaining portion of the kit 300 containing the filter 306 is removed and discarded. A remnant of the tubing 305 remains connected to the container 302.

The container 302 holding the methylene blue and leukocyte-reduced plasma, and carrying a remnant of the tubing section 305, is placed into a white light chamber 356 (see FIG. 9). The chamber 356 comprises twelve fluorescent lamps 358, which supply output in the visible range (400 to 700 nm) to both sides of the container 302. The chamber 356 monitors the light intensity adjusts exposure time to control total light dosage delivered to the container 306. The light activates the methylene blue to release singlet oxygen, which inactivates viruses in the plasma. The approximate time of illumination to deliver a targeted dose of 3.3 J per $cm^3$ is 30 minutes. Further details of a light chamber can be found in Wolf et al. U.S. Pat. No. 5,290,221 and Bischof et al. U.S. Pat. No. 5,300,019.

After the illumination step, the leukocyte-reduced plasma is frozen within the container 302 at less than −30° C. for storage using conventional blood bank practices. The plasma within the container 302 is thawed when fractionation or transfusion is required.

In the illustrated embodiment (see FIG. 1), the kit 300 includes written instructions 374 for using the kit for its intended purpose. The instructions 374 direct the technician to handle the kit in a prescribed way to best accomplish the desired therapeutic objectives, as set forth in the preceding description and shown in FIGS. 7 to 9.

The instructions 374 may take various forms. Representative instructions 374 direct the technician, upon removal of the overwrap 328, to convey plasma through the tubing 304 from the source 338 through the filter 306 to separate leukocytes from the plasma. The representative instructions 374 also direct the technician to convey leukocyte-reduced plasma through the tubing 304 from the filter 306 to the transfer container 302. The representative instructions 374 also instruct the technician to mix the photoactivated material 326 with the plasma and to expose leukocyte-reduced plasma mixed with the photoactive material 326 to light that activates the photoactive material 326. The representative instructions 374 also direct the technician to store the plasma in the container 302 after the photoactivation process.

The instructions 374 can, of course, include further details based upon the particular configuration of the kit 300. For example, in the context of the kit 300 shown in FIG. 1, the instructions 374 can direct the technician to mix the photoactivated material with leukocyte-reduced plasma within in the container chamber 320. In this context, the instructions 374 can also direct the technician to expose the container chamber 320 to light that activates the photoactive material 326 mixed within the chamber 320 with the leukocyte-reduced plasma. The instructions 374 can also direct the technician to vent air from the container chamber 320 in a path that bypasses the filter 306, which in FIG. 1 comprises the branch tubing 308. The instructions 374 can also instruct the technician to flush the tubing 304 downstream of the filter 306 with plasma and photoactive material 326 from the chamber 320.

EXAMPLE

A study was conducted to demonstrate the ability of the kit 300 when used in accordance with the instructions 374 to inactivate viruses under intended use conditions. In the study, a maximum plasma volume of 310 mL was employed to provide the lowest concentration of methylene blue and the greatest fluid thickness to be illuminated. In addition, the nominal targeted light dose of 33 $J/cm^2$ was reduced to 24 or 30 $J/cm^2$ to further stress the study conditions.

Plasma was collected from CPD anticoagulated whole blood units following routine blood bank procedures, yielding plasma that is essentially free of red blood cells. The plasma was not frozen prior to treatment during the study.

A panel of viruses was selected to represent the most significant agents that can contaminate fresh frozen plasma and to represent a broad spectrum of physical/chemical forms of viruses (i.e., lipid enveloped and non-lipid enveloped RNA and DNA viruses, as well as intra-cellular viruses). The panel included the following viruses: BVDV (strain Singer); HIV Type 1 (HIV-1, strain $III_8$); human herpes simplex virus Type 1 (HSV-1, strain MacIntyre); pseudorabies virus (PRV, strain Aujeszky); simian virus Type 40 (SV-40, strain Pa-57); duck hepatitis B DHBV; and cell associated HIV (H-9/HIV, HIV $III_8$ chronically infected H-9 cells).

These viruses were added to units of plasma before treatment in physiologically representative concentrations. A process control comprising an aliquot of virus-spiked plasma, was collected from each unit prior to processing in the kit 300. The process control served as the baseline value for the calculation of the virus load reduction, called the log reduction value (LRV). LRV represents either (i) the difference in log virus titers between the process control and the processed sample, or (ii) the difference in log virus titers between the process control and the validated sensitivity limit of the assay, if there was no recoverable virus (indicated by the use of the symbol ">" in the Table 1 below).

The virus panel and the log reduction values (LRV's) obtained by processing the plasma in the kit 300 in accordance with the instructions 374 are summarized in the following Table 1:

TABLE 1

Results of Study on Viral Inactivation Using the Kit 300

| Virus | Model for | Size (nm) | LRV |
|---|---|---|---|
| HIV | Self | 110 | >6.6 at 24 $J/cm^2$ |
| BVDV | HCV | 60–70 | >5.93 ± 0.07 at 24 $J/cm^2$ |
| DHBV | HBV | 40 | 3.5 at 30 $J/cm^2$ |
| PRV | enveloped DNA virus | 150–180 | 5.52 ± 0.38 at 30 $J/cm^2$ |
| HSV | enveloped DNA virus | 150–180 | >6.16 ± 0.06 at 24 $J/cm^2$ |
| SV-40 | non-enveloped DNA virus | 55 | 4.27 ± 0.30 at 24 $J/cm^2$ |

TABLE 1-continued

Results of Study on Viral
Inactivation Using the Kit 300

| Virus | Model for | Size (nm) | LRV |
|---|---|---|---|
| HIV/H9 | virus-infected leukocytes | | No Recoverable Viruses after challenge with 1 × 10$^8$ HIV/H9 cells |

Table 1 demonstrates that use of the kit 300 is effective against small and large lipid enveloped viruses with either RNA or DNA genomes. Table 1 also demonstrates the capability of the kit 300 to inactivate certain non-enveloped viruses, which are not resistant to the virucidal action of methylene blue (for example, non-enveloped encephalomyocarditis virus (EMC) has demonstrated a resistance to the virucidal action of methylene blue).

The kit 300 provides more reliability and ease of use than the removal of leukocytes from plasma by lysing using conventional freeze-thaw processes. The kit 300 also provides greater removal of adventitious agents (i.e., viruses) than mere light inactivation (which does not remove intracellular agents) and/or bed-side filtering of plasma (which only removes fibrin clots, and not leukocytes).

Figure 11:
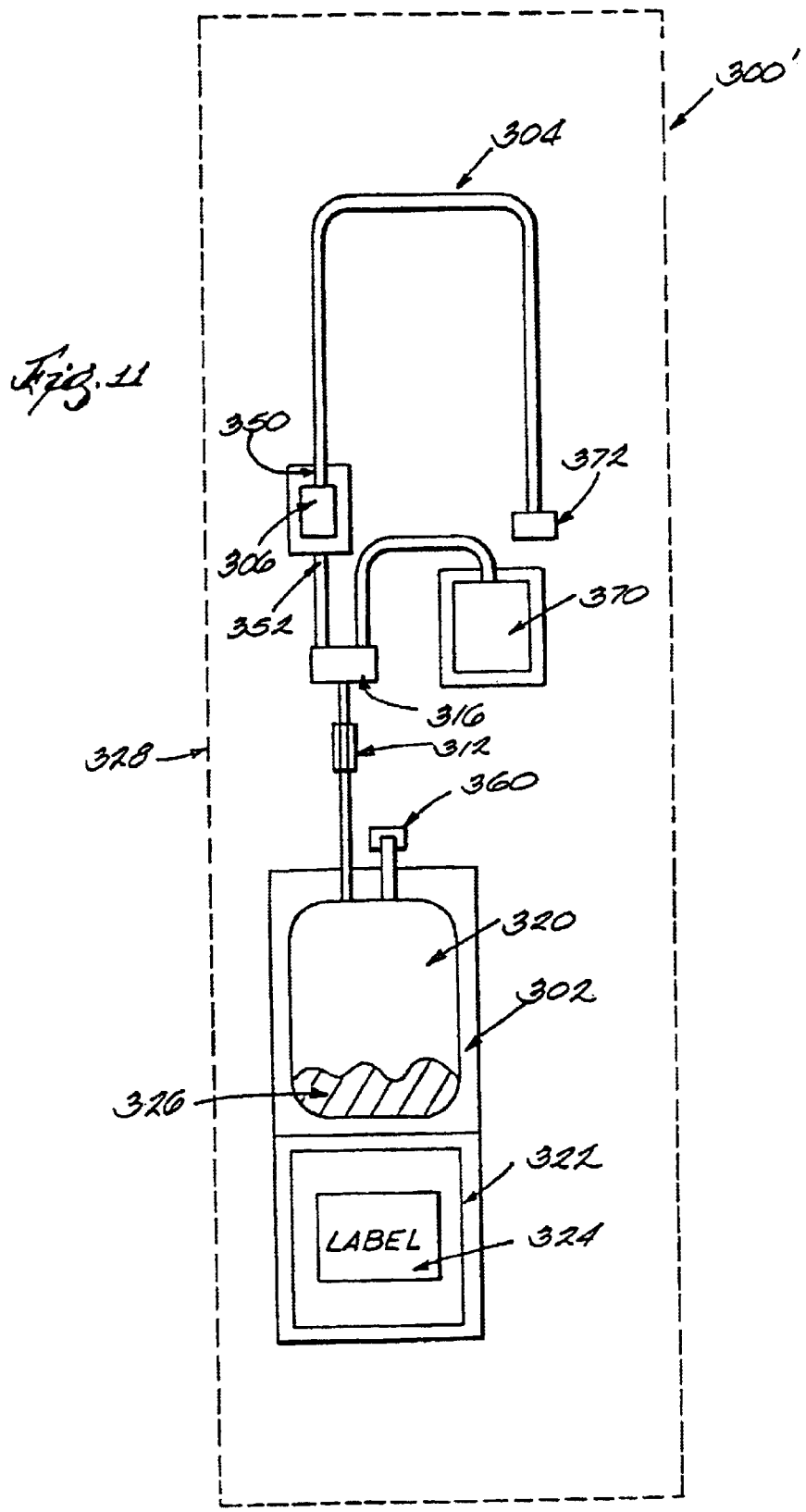
FIG. 11 is a plane view of an alternative embodiment of a blood processing and storage kit for reducing the presence of viral agents in plasma, which includes an integrally attached air reservoir.

FIG. 11 shows, as an alternative embodiment, a kit 300' sharing many of the component parts of the kit 300 shown in FIG. 1. The common elements (which are assigned the same reference numbers as in FIG. 1) include the processing and storage container 302, the transfer tubing 304, the filter 306, the photoactive material 326, and the frangible cannula 312.

However, the kit 300' shown in FIG. 11 does not include the branch tubing 308 and the air pillow 310.

Instead, the far end of the tubing 304 in the kit 300' is closed by a plug 372. The kit 300' also includes an air reservoir 370 integrally connected to the tubing 304 by the Y-connector 316 between the filter 306 and the container 302.

The air reservoir 370 takes the place of the air pillow 310. Like the pillow 310, the reservoir 370 contains a residual amount of air to prevent collapse of the tubing 304 during steam sterilization. The reservoir 370 also serves as a chamber to receive vented air and residual plasma from the container 302 at the end of the filtration process.

More particularly, using the kit 300', plasma from the source container 338 is passed for leukocyte reduction through the filter 306 and mixed with the photoactive material 326 in the container 320 in the same manner previously described and shown in FIG. 7.

Figure 12A:
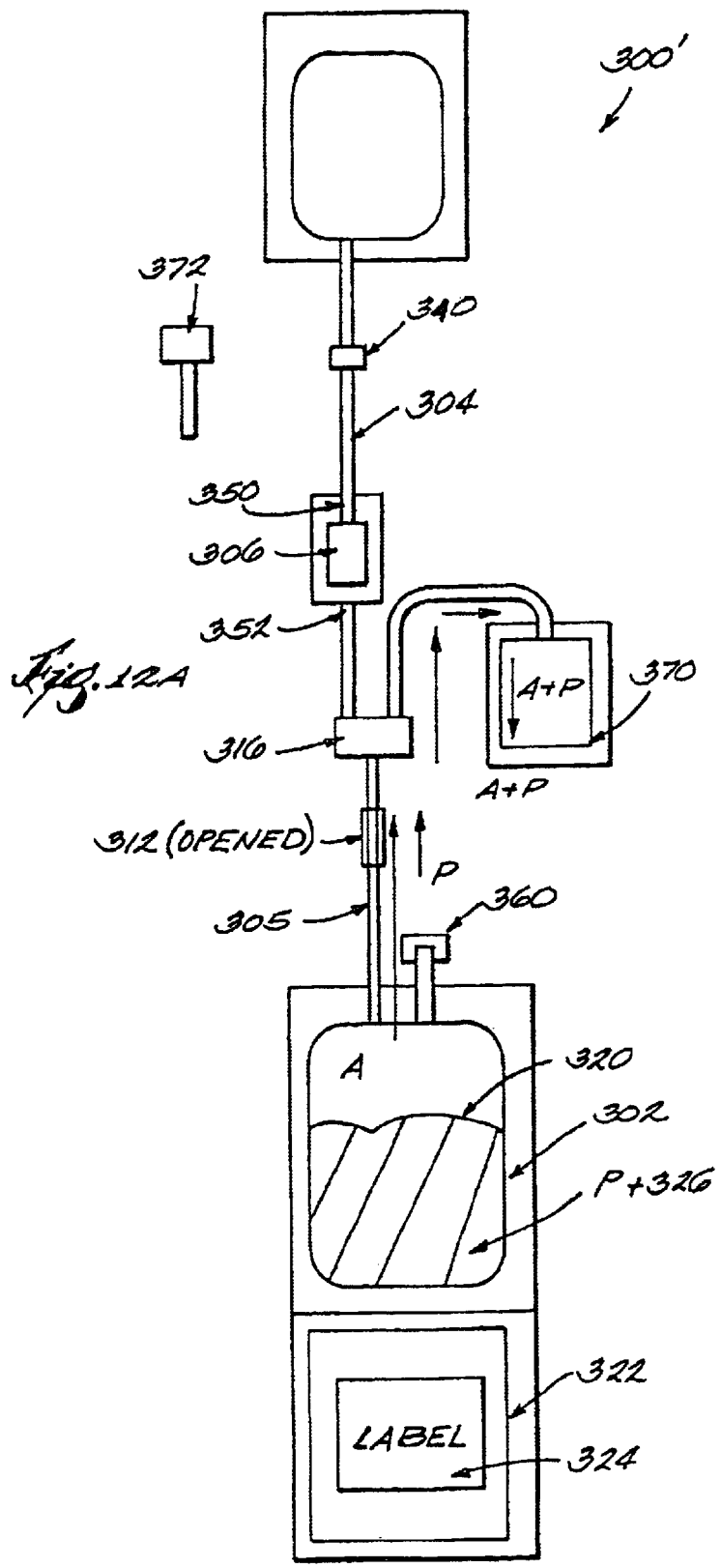
FIG. 12A is a plane view of the kit shown in FIG. 11 being use to vent air and residual plasma from the processing and storage container into the air reservoir.

As FIG. 12A shows, after filtration and mixing, air A is vented from the container 302 into the reservoir 370. Residual plasma P is also displaced out of the tubing section 305 and into the reservoir 370. As FIG. 12B shows, as air venting proceeds, an amount of the mixture M of photoactive material 326 and plasma P will enter the section 305 of the transfer tubing 304 between the filter 306 and the container 302. The mixture M flushes this section of the transfer tubing 304 with the photoactive material 326 and plasma mixture.

In all other respects the process for handling the kit 300' is the same as previously described with respect to the kit 300.

FIG. 13 shows, as another alternative embodiment, a kit 30' sharing many of the component parts of the kit 300 shown in FIG. 1. The common elements (which are assigned the same reference numbers as in FIG. 1) include the processing and storage container 302, the transfer tubing 304, the branch tubing 308, the filter 306, the photoactive material 326, the air pillow 310, and the frangible cannula 312. The kit 300" shown in FIG. 13 includes an additional in-line filter 376 in the transfer tubing 304 downstream of the filter 306. The filter 376 includes a filter media 378 that removes from plasma a second cellular species different than the species removed by the filter media 307, which second cellular species does actually or potentially entrain viral agents. In the illustrated and preferred embodiment, where the principal cellular species targeted by the filter media 307 are leukocytes, the second cellular species targeted by the second filter media 378 are platelets.

As described above in connection with the filter media 307, the pore size of the filter media 378 can be tailored to remove platelets from plasma by exclusion. It is believed that candidate materials for the media 307 formed with a pore size range of between 0.3 μm and 0.45 μcm (which is smaller than the pore size range of the media 307) will serve to remove platelets from plasma by exclusion.

The presence of the second, downstream media 378, having a smaller pore size than the first, upstream media 307, also provides added assurance that the cellular species targeted for removal by the first media 307 (i.e., leukocytes) will, in fact, be depleted or essentially depleted from the plasma. In this respect, the smaller pore size media 378 serves both a redundant function of removing leukocytes and an added second step function of removing the smaller platelet species.

It should be appreciated that the second filter media 378 can, instead of being separately housed as the filter 378, be integrated as another layer with the already multi-layer filter media 307.

In all other respects the process for handling the kit 300" is the same as previously described with respect to the kit 300.

Features and advantages of the invention are set forth in the following claims.

We claim:

1. A kit comprising tubing adapted to be coupled to a blood constituent source to convey blood constituent, a source of photoactive material to be mixed with the blood constituent, a transfer container coupled to the tubing, the transfer container including a wall made of a material that is transparent to light that activates the photoactive material, and a removable overwrap separate from the wall of the container, the overwrap enveloping the source of photoactive material within the kit said overwrap including a light filtering material that is not transparent to light in the activating spectrum for said photoactive material thereby preventing degradation of the photoactive material prior to removal of the overwrap.

2. A kit according to claim 1 wherein the photoactive material includes methylene blue.

3. A kit according to claim 2
wherein the light filtering material includes a blue material.

4. A kit according to claim 3
wherein the blue material includes phtalocyanine pigments.

5. A kit according to claim 1
wherein the photoactive material includes psoralen.

6. A kit according to claim 5
wherein the light filtering material includes a red material.

7. A kit according to claim 1
wherein the overwrap envelops the entire kit.

8. A kit according to claim 1 further including
wherein the tubing includes a first filtration media to separate a first cellular blood species from the blood constituent conveyed from the blood constituent source, and wherein the tubing also includes a second filtration media in series with the first filtration media to second cellular blood species from the blood constituent conveyed from the blood constituent source, to thereby produce a filtered blood constituent that is essentially free of the first and second cellular blood species.

* * * * *